(12) United States Patent
Kjeldsen (10) Patent No.: US 7,105,314 B2
(45) Date of Patent: Sep. 12, 2006

(54) METHOD FOR MAKING HUMAN INSULIN PRECURSORS

(75) Inventor: Thomas Borglum Kjeldsen, Virum (DK)

(73) Assignee: Novo Nordisk A/S, Bagsvaerd (DK)

( * ) Notice: Subject to any disclaimer, the term of this patent is extended or adjusted under 35 U.S.C. 154(b) by 0 days.

(21) Appl. No.: 10/114,557

(22) Filed: Apr. 1, 2002

(65) Prior Publication Data

US 2005/0059119 A1 Mar. 17, 2005

Related U.S. Application Data

(60) Provisional application No. 60/283,763, filed on Apr. 13, 2001.

(30) Foreign Application Priority Data

Apr. 2, 2001 (DK) ............................... 2001 00547

(51) Int. Cl.
*A61K 38/28* (2006.01)
*C07K 14/62* (2006.01)
*C12N 1/16* (2006.01)
*C12N 15/17* (2006.01)
*C12N 15/63* (2006.01)

(52) U.S. Cl. ..................... 435/69.1; 435/325; 435/243; 435/255.1; 435/320.1; 514/3; 514/866; 530/303

(58) Field of Classification Search ................ 530/303; 514/3
See application file for complete search history.

(56) References Cited

U.S. PATENT DOCUMENTS

| 4,916,212 A | 4/1990 | Markussen et al. |
| 5,304,473 A * | 4/1994 | Belagaje et al. ........... 435/69.7 |
| 5,324,641 A | 6/1994 | Jonassen et al. |
| 5,840,542 A | 11/1998 | King et al. |
| 5,962,267 A | 10/1999 | Shin et al. |

FOREIGN PATENT DOCUMENTS

| EP | 0 055 945 A2 | 7/1982 |
| EP | 0 163 529 A1 | 12/1985 |
| EP | 0 347 845 A2 | 12/1989 |
| EP | 0 347 845 B1 | 12/1989 |
| EP | 0 741 188 A2 | 11/1996 |
| WO | WO 95/16708 | 6/1995 |
| WO | WO 01/49742 A1 | 7/2001 |

OTHER PUBLICATIONS

Pfeffer et al., Ann. Rev. Biochem, vol. 56, pp. 829-852 (1987).
Frank et al., Pierce Chemical Co., Rockford, IL, U.S.A., pp. 729-739 (1981).
Thim et al., Proc. Natl. Acad. Sci. U.S.A., vol. 83, pp. 6766-6770 (1986).
Chan et al., Proc. Natl. Acad. Sci. U.S.A., vol. 78, pp. 5401-5405 (1981).

* cited by examiner

*Primary Examiner*—Christine J. Saoud
(74) *Attorney, Agent, or Firm*—Reza Green; Len S. Smith; Richard Bork (57) ABSTRACT

Novel insulin precursors comprising a connecting peptide (mini C-peptide) of preferably up to 6 amino acid residues and comprising at least one Pro are provided. The precursors can be converted into human insulin or desB30 human insulin.

37 Claims, 3 Drawing Sheets

FIG. 1

```
                                                                    EcoRI
                                                                  ~~~~~~~
 901   TTCTTGCTTA AATCTATAAC TACAAAAAAC ACATACAGGA ATTCCATTCA
       AAGAACGAAT TTAGATATTG ATGTTTTTTG TGTATGTCCT TAAGGTAAGT

951   AGAATAGTTC AAACAAGAAG ATTACAAACT ATCAATTTCA TACACAATAT
       TCTTATCAAG TTTGTTCTTC TAATGTTTGA TAGTTAAAGT ATGTGTTATA

+1                    M   K   L   K   T   V   R   S   A   V   L   S
                                                   BglII
                                                   ~~~~~~
1001   AAACGATTAA AAGAATGAAA CTGAAAACTG TAAGATCTGC GGTCCTTTCG
       TTTGCTAATT TTCTTACTTT GACTTTTGAC ATTCTAGACG CCAGGAAAGC

+1    S   L   F   A   S   Q   V   L   G   Q   P   I   D   D   T   E   S
                                       MscI
                                       ~~~~~~
1051   TCACTCTTTG CATCTCAGGT CCTTGGCCAA CCAATTGACG ACACTGAATC
       AGTGAGAAAC GTAGAGTCCA GGAACCGGTT GGTTAACTGC TGTGACTTAG

+1    Q   T   T   S   V   N   L   M   A   D   D   T   E   S   A   F
1101   TCAAACTACT TCTGTCAACT TGATGGCTGA CGACACTGAA TCTGCTTTCG
       AGTTTGATGA AGACAGTTGA ACTACCGACT GCTGTGACTT AGACGAAAGC

+1  A   T   Q   T   N   S   G   L   D   V   V   G   L   I   S   M
                                                                   NcoI
                                                                   ~~~~~
1151   CTACTCAAAC TAACTCTGGT GGTTTGGATG TTGTTGGTTT GATCTCCATG
       GATGAGTTTG ATTGAGACCA CCAAACCTAC AACAACCAAA CTAGAGGTAC

+1    A   K   R   E   E   G   E   P   K   F   V   N   Q   H   L   C   G
       NcoI                                    HpaI
       ~                                       ~~~~~~
1201   GCTAAGAGAG AAGAAGGTGA ACCAAAGTTC GTTAACCAAC ACTTGTGCGG
       CGATTCTCTC TTCTTCCACT TGGTTTCAAG CAATTGGTTG TGAACACGCC

+1    S   H   L   V   E   A   L   Y   L   V   C   G   E   R   G   F
                   HindIII
                   ~~~~~~
1251   TTCCCACTTG GTTGAAGCTT TGTACTTGGT TTGCGGTGAA AGAGGTTTCT
       AAGGGTGAAC CAACTTCGAA ACATGAACCA AACGCCACTT TCTCCAAAGA +1    F   Y   T   P   K   A   A   K   G   I   V   E   Q   C   C   T   S
                   Bsu36I
                   ~~~~~~~~
1301   TCTACACTCC TAAGGCTGCT AAGGGTATTG TCGAACAATG CTGTACCTCC
       AGATGTGAGG ATTCCGACGA TTCCCATAAC AGCTTGTTAC GACATGGAGG
```

FIG. 2

```
      +1  I   C   S   L   Y   Q   L   E   N   Y   C   N   *
    1351  ATCTGCTCCT TGTACCAATT GGAAAACTAC TGCAACTAGA CGCAGCCCGC
          TAGACGAGGA ACATGGTTAA CCTTTTGATG ACGTTGATCT GCGTCGGGCG
                XbaI
                ~~~~~~
    1401  AGGCTCTAGA AACTAAGATT AATATAATTA TATAAAAATA TTATCTTCTT
          TCCGAGATCT TTGATTCTAA TTATATTAAT ATATTTTTAT AATAGAAGAA
```

FIG 2 (CONT.)

METHOD FOR MAKING HUMAN INSULIN PRECURSORS

CROSS REFERENCE TO RELATED APPLICATIONS

This application claims priority under 35 U.S.C. 119 of Danish application no. PA 2001 00547 filed on Apr. 2, 2001 and U.S. provisional application No. 60/283,763 filed on Apr. 13, 2001, the contents of which are fully incorporated herein by reference.

BACKGROUND

Yeast organisms produce a number of proteins that have a function outside the cell. Such proteins are referred to as secreted proteins. These secreted proteins are expressed initially inside the cell in a precursor or a pre-form containing a pre-peptide sequence ensuring effective direction (translocation) of the expressed product across the membrane of the endoplasmic reticulum (ER). The pre-peptide, normally named a signal peptide, is generally cleaved off from the desired product during translocation. Once entered in the secretory pathway, the protein is transported to the Golgi apparatus. From the Golgi, the protein can follow different routes that lead to compartments such as the cell vacuole or the cell membrane, or it can be routed out of the cell to be secreted to the external medium (Pfeffer et al. (1987) Ann. Rev. Biochem. 56:829–852).

Insulin is a polypeptide hormone secreted by β-cells of the pancreas and consists of two polypeptide chains, A and B, which are linked by two inter-chain disulphide bridges. Furthermore, the A-chain features one intra-chain disulphide bridge.

The hormone is synthesized as a single-chain precursor proinsulin (preproinsulin) consisting of a prepeptide of 24 amino acid followed by proinsulin containing 86 amino acids in the configuration: prepeptide-B-Arg Arg-C-Lys Arg-A, in which C is a connecting peptide of 31 amino acids. Arg-Arg and Lys-Arg are cleavage sites for cleavage of the connecting peptide from the A and B chains.

Three major methods have been used for the production of human insulin in microorganisms. Two involve *Escherichia coli*, with either the expression of a large fusion protein in the cytoplasm (Frank et al. (1981) in Peptides: Proceedings of the 7$^{th}$ American Peptide Chemistry Symposium (Rich & Gross, eds.), Pierce Chemical Co., Rockford, Ill. pp 729–739), or use of a signal peptide to enable secretion into the periplasmic space (Chan et al. (1981) PNAS 78:5401–5404). A third method utilizes *Saccharomyces cerevisiae* to secrete an insulin precursor into the medium (Thim et al. (1986) PNAS 83:6766–6770). The prior art discloses a limited number of insulin precursors which are expressed in either *E. coli* or *Saccharomyces cerevisiae*, vide U.S. Pat. No. 5,962,267, WO 95/16708, EP 0055945, EP 0163529, EP 0347845 and EP 0741188.

SUMMARY OF THE INVENTION

The present invention features novel connecting peptides (C-peptides) which confer an increased production yield of insulin precursor molecules when expressed in a transformed microorganism, in particular yeast. Such insulin precursors can then be converted into human insulin, desB30 human insulin or certain acylated human insulins by one or more suitable, well known conversion steps.

The connecting peptides of the present invention contain at least one Pro and will generally be relatively short, typically not longer than 10 amino acid residues in length and preferably not more than 6–4 amino acid residues in length.

The connecting peptide will contain a cleavage site at its C-terminal end enabling in vitro cleavage of the connecting peptide from the A chain. Such cleavage site may be any convenient cleavage site known in the art, e.g. a Met cleavable by cyanogen bromide; a single basic amino acid residue or a pair of basic amino acid residues (Lys or Arg) cleavable by trypsin or trypsin like proteases; *Acromobactor lyticus* protease or by a carboxypeptidase protease. The cleavage site enabling cleavage of the connecting peptide from the A-chain is preferably a single basic amino acid residue Lys or Arg, preferably Lys.

Cleavage of the connecting peptide from the B chain is enabled by cleavage at the natural $Lys^{B29}$ amino acid residue in the B chain giving rise to a desB30 insulin precursor. If the insulin precursor is to be converted into human insulin, the B30 Thr amino acid residue (Thr) can then be added by well known in vitro, enzymatic procedures. The desB30 insulin may also be converted into an acylated insulin as disclosed in U.S. Pat. No. 5,750,497 and U.S. Pat. No. 5,905,140.

In one embodiment the connecting peptide will not contain two adjacent basic amino acid residues (Lys,Arg). In this embodiment, cleavage from the A-chain will preferably be accomplished at a single Lys or Arg located at the N-terminal end of the A-chain.

In another embodiment of the present invention the Pro is immediately N-terminal to the cleavage site adjacent to the A chain. The connecting peptide may contain more than one Pro, but preferably not more than three Pro residues.

Accordingly, in one aspect the present invention relates to insulin precursors comprising a connecting peptide (C-peptide) being cleavable from the A and B chains and comprising at least one Pro and a cleavage site enabling cleavage of the peptide bond between the A-chain and the connecting peptide, wherein one Pro is immediately N-terminal to said cleavage site.

In another aspect the present invention relates to insulin precursors comprising a connecting peptide (C-peptide) being cleavable from the A and B chains and consisting of up to 6 amino acid residues of which at least one is a Pro.

In a further aspect, the present invention is related to insulin precursors comprising the formula:

B(1–29)-$X_1$-Y-A(1–21)

wherein $X_1$, is a peptide sequence of 1–5 amino acid residues comprising at least one Pro, and Y is a cleavage site.

In one embodiment, the total number of amino acid residues in $X_1$ will be from 1–4, 1–3, or 1–2 amino acid residues. The amino acid residues in X, can be any codable amino acid residue and may be the same or different with the only proviso that at least one is Pro.

In a further embodiment Y is Met or a dibasic amino acid sequence, LysLys, ArgArg, ArgLys or LysArg. In a still further embodiment Y is a single basic amino acid residue, Lys or Arg.

In a further embodiment the sequence $X_1$-Y will not contain two adjacent basic amino acid residues (Lys, Arg) and in a still further embodiment $X_1$ will contain an amino acid residue with a free COOH group (Glu, Asp) or an amino acid residue with a free amino group (Gln, Asn, His).

Examples of $X_1$-Y-sequences are GlnProLys; ThrProLys; GluProLys; GlyProLys; MetProLys; SerProLys; AspProLys; AlaAspProLys (SEQ ID NO:8); AsnAspProLys (SEQ ID NO:9); GluAspProLys (SEQ ID NO:10) and AlaAspProLys (SEQ ID NO:11).

The present invention is also related to polynucleotide sequences which code for the claimed insulin precursors. In a further aspect the present invention is related to vectors containing such polynucleotide sequences and host cells containing such polynucleotide sequences or vectors.

In another aspect, the invention relates to a method for producing the insulin precursors in a host cell, said method comprising (i) culturing a host cell comprising a polynucleotide sequence encoding the insulin precursors of the invention under suitable conditions for expression of said insulin precursor; and (ii) isolating the insulin precursor from the culture medium.

In still a further aspect, the invention relates to a process for producing desB30 human insulin or human insulin comprising (i) culturing a host cell comprising a polynucleotide sequence encoding an insulin precursor of the invention; (ii) isolating the insulin precursor from the culture medium and (iii) converting the insulin precursor into desB30 human insulin or human insulin by in vitro enzymatic conversion.

In still a further aspect, the invention relates to a process for producing an acylated desB30 human insulin comprising (i) culturing a host cell comprising a polynucleotide sequence encoding an insulin precursor of the invention; (ii) isolating the insulin precursor from the culture medium, (iii) converting the insulin precursor into desB30 human insulin and (iv) converting the desB30 human insulin into an acylated derivate by use of a convenient acylation method.

In one embodiment of the present invention the host cell is a yeast host cell and in a further embodiment the yeast host cell is selected from the genus *Saccharomyces*. In a further embodiment the yeast host cell is selected from the species *Saccharomyces cerevisiae*.

DETAILED DESCRIPTION

Abbreviations and Nomenclature.

By "connecting peptide" or "C-peptide" is meant the connection moiety "C" of the B-C-A polypeptide sequence of a single chain preproinsulin-like molecule. Specifically, in the natural insulin chain, the C-peptide connects position 30 of the B chain and position 1 of the A chain. A "mini C-peptide" or "connecting peptide" such as those described herein, connect B29 to A1 and differ in sequence and length from that of the natural C-peptide.

By "IP" is meant a single-chain insulin precursor in which a desB30 chain is linked to the A chain of insulin via a connecting peptide. The single-chain insulin precursor will contain correctly positioned disulphide bridges (three) as in human insulin.

With "desB30" or "B(1–29)" is meant a natural insulin B chain lacking the B30 amino acid residue and "A(1–21)" means the natural insulin A chain. The mini C-peptide and its amino acid sequence are indicated in the three letter amino acid code.

By "insulin precursor" is meant a single-chain polypeptide which by one or more subsequent chemical and/or enzymatic processes can be converted into human insulin or desB30 human insulin.

The term "immediately N-terminal to" is meant to illustrate the situation where an amino acid residue or a peptide sequence is directly linked at its C-terminal end to the N-terminal end of another amino acid residue or amino acid sequence by means of a peptide bond.

The present invention features novel mini C-peptides connecting position 29 of the insulin B chain and position 1 of the insulin A chain which significantly increased production yields in a yeast host cell. By the term "significantly increased production," "increased fermentation yield," and the like, is meant an increase in secreted amount of the insulin precursor molecule present in the culture supernatant compared to the yield of an insulin precursor with a C peptide different from the C peptides according to the present invention. An "increased" fermentation yield is an absolute number larger than the control; preferably, the increase is 50% or more larger than the control; even more preferably, the increase is 100% or more larger than control levels.

"POT" is the *Schizosaccharomyces pombe* triose phosphate isomerase gene, and "TPI1" is the *S. cerevisiae* triose phosphate isomerase gene.

By a "leader" is meant an amino acid sequence consisting of a pre-peptide (the signal peptide) and a pro-peptide.

The term "signal peptide" is understood to mean a pre-peptide which is present as an N-terminal sequence on the precursor form of a protein. The function of the signal peptide is to allow the heterologous protein to facilitate translocation into the endoplasmic reticulum. The signal peptide is normally cleaved off in the course of this process. The signal peptide may be heterologous or homologous to the yeast organism producing the protein. A number of signal peptides which may be used with the DNA construct of the invention including yeast aspartic protease 3 (YAP3) signal peptide or any functional analog (Egel-Mitani et al. (1990) YEAST 6:127–137 and U.S. Pat. No. 5,726,038) and the α-factor signal of the MFα1 gene (Thorner (1981) in *The Molecular Biology of the Yeast Saccharomyces cerevisiae*, Strathern et al., eds., pp 143–180, Cold Spring Harbor Laboratory, NY and U.S. Pat. No. 4,870,00.

The term "pro-peptide" means a polypeptide sequence whose function is to allow the expressed polypeptide to be directed from the endoplasmic reticulum to the Golgi apparatus and further to a secretory vesicle for secretion into the culture medium (i.e. exportation of the polypeptide across the cell wall or at least through the cellular membrane into the periplasmic space of the yeast cell). The pro-peptide may be the yeast α-factor pro-peptide, vide U.S. Pat. Nos. 4,546,082 and 4,870,008. Alternatively, the pro-peptide may be a synthetic pro-peptide, which is to say a pro-peptide not found in nature. Suitable synthetic pro-peptides are those disclosed in U.S. Pat. Nos. 5,395,922; 5,795,746; 5,162,498 and WO 98/32867. The pro-peptide will preferably contain an endopeptidase processing site at the C-terminal end, such as a Lys-Arg sequence or any functional analog thereof.

The polynucleotide sequence of the invention may be prepared synthetically by established standard methods, e.g. the phosphoamidite method described by Beaucage et al.

(1981) Tetrahedron Letters 22:1859–1869, or the method described by Matthes et al. (1984) EMBO Journal 3:801–805. According to the phosphoamidite method, oligonucleotides are synthesized, for example, in an automatic DNA synthesizer, purified, duplexed and ligated to form the synthetic DNA construct. A currently preferred way of preparing the DNA construct is by polymerase chain reaction (PCR).

The polynucleotide sequence of the invention may also be of mixed genomic, cDNA, and synthetic origin. For example, a genomic or cDNA sequence encoding a leader peptide may be joined to a genomic or cDNA sequence encoding the A and B chains, after which the DNA sequence may be modified at a site by inserting synthetic oligonucleotides encoding the desired amino acid sequence for homologous recombination in accordance with well-known procedures or preferably generating the desired sequence by PCR using suitable oligonucleotides.

The invention encompasses a vector which is capable of replicating in the selected microorganism or host cell and which carries a polynucleotide sequence encoding the insulin precursors of the invention. The recombinant vector may be an autonomously replicating vector, i.e., a vector which exists as an extra-chromosomal entity, the replication of which is independent of chromosomal replication, e.g., a plasmid, an extra-chromosomal element, a mini-chromosome, or an artificial chromosome. The vector may contain any means for assuring self-replication. Alternatively, the vector may be one which, when introduced into the host cell, is integrated into the genome and replicated together with the chromosome(s) into which it has been integrated. Furthermore, a single vector or plasmid or two or more vectors or plasmids which together contain the total DNA to be introduced into the genome of the host cell, or a transposon may be used. The vector may be linear or closed circular plasmids and will preferably contain an element(s) that permits stable integration of the vector into the host cell's genome or autonomous replication of the vector in the cell independent of the genome.

In a preferred embodiment, the recombinant expression vector is capable of replicating in yeast. Examples of sequences which enable the vector to replicate in yeast are the yeast plasmid 2 μm replication genes REP 1–3 and origin of replication.

The vectors of the present invention preferably contain one or more selectable markers which permit easy selection of transformed cells. A selectable marker is a gene the product of which provides for biocide or viral resistance, resistance to heavy metals, prototrophy to auxotrophs, and the like. Examples of bacterial selectable markers are the dal genes from *Bacillus subtilis* or *Bacillus licheniformis*, or markers which confer antibiotic resistance such as ampicillin, kanamycin, chloramphenicol or tetracycline resistance. Selectable markers for use in a filamentous fungal host cell include amdS (acetamidase), argB (ornithine carbamoyltransferase), pyrG (orotidine-5'-phosphate decarboxylase) and trpC (anthranilate synthase. Suitable markers for yeast host cells are ADE2, HIS3, LEU2, LYS2, MET3, TRP1, and URA3. A preferred selectable marker for yeast is the *Schizosaccharomyces pompe* TPI gene (Russell (1985) Gene 40:125–130).

In the vector, the polynucleotide sequence is operably connected to a suitable promoter sequence. The promoter may be any nucleic acid sequence which shows transcriptional activity in the host cell of choice including mutant, truncated, and hybrid promoters, and may be obtained from genes encoding extra-cellular or intra-cellular polypeptides either homologous or heterologous to the host cell.

Examples of suitable promoters for directing the transcription in a bacterial host cell, are the promoters obtained from the *E. coli* lac operon, *Streptomyces coelicolor* agarase gene (dagA), *Bacillus subtilis* levansucrase gene (sacB), *Bacillus licheniformis* alpha-amylase gene (amyL), *Bacillus stearothermophilus* maltogenic amylase gene (amyM), *Bacillus amyloliquefaciens* alpha-amylase gene (amyQ), and *Bacillus licheniformis* penicillinase gene (penP). Examples of suitable promoters for directing the transcription in a filamentous fungal host cell are promoters obtained from the genes for *Aspergillus oryzae* TAKA amylase, *Rhizomucor miehei* aspartic proteinase, *Aspergillus niger* neutral alpha-amylase, and *Aspergillus niger* acid stable alpha-amylase. In a yeast host, useful promoters are the *Saccharomyces cerevisiae* Ma1, TPI, ADH or PGK promoters.

The polynucleotide construct of the invention will also typically be operably connected to a suitable terminator. In yeast a suitable terminator is the TPI terminator (Alber et al. (1982) J. Mol. Appl. Genet. 1:419–434).

The procedures used to ligate the polynucleotide sequence of the invention, the promoter and the terminator, respectively, and to insert them into a suitable vector containing the information necessary for replication in the selected host, are well known to persons skilled in the art. It will be understood that the vector may be constructed either by first preparing a DNA construct containing the entire DNA sequence encoding the insulin precursors of the invention, and subsequently inserting this fragment into a suitable expression vector, or by sequentially inserting DNA fragments containing genetic information for the individual elements (such as the signal, pro-peptide, mini C-peptide, A and B chains) followed by ligation.

The present invention also relates to recombinant host cells, comprising a polynucleotide sequence encoding the insulin precursors of the invention. A vector comprising such polynucleotide sequence is introduced into the host cell so that the vector is maintained as a chromosomal integrant or as a self-replicating extra-chromosomal vector as described earlier. The term "host cell" encompasses any progeny of a parent cell that is not identical to the parent cell due to mutations that occur during replication. The host cell may be a unicellular microorganism, e.g., a prokaryote, or a non-unicellular microorganism, e.g., a eukaryote. Useful unicellular cells are bacterial cells such as gram positive bacteria including, but not limited to, a *Bacillus* cell, *Streptomyces* cell, or gram negative bacteria such as *E. coli* and *Pseudomonas* sp. Eukaryote cells may be mammalian, insect, plant, or fungal cells. In a preferred embodiment, the host cell is a yeast cell. The yeast organism used in the process of the invention may be any suitable yeast organism which, on cultivation, produces large amounts of the insulin precursor and insulin precursor analogs of the invention. Examples of suitable yeast organisms are strains selected from the yeast species *Saccharomyces cerevisiae*, *Saccharomyces kluyveri*, *Schizosaccharomyces pombe*, *Sacchoromyces uvarum*, *Kluyveromyces lactis*, *Hansenula polymorpha*, *Pichia pastoris*, *Pichia methanolica*, *Pichia kluyveri*, *Yarrowia lipolytica*, *Candida* sp., *Candida utilis*, *Candida cacaoi*, *Geotrichum* sp., and *Geotrichum fermentans*.

The transformation of the yeast cells may for instance be effected by protoplast formation followed by transformation in a manner known per se. The medium used to cultivate the cells may be any conventional medium suitable for growing yeast organisms. The secreted insulin precursor of the invention, a significant proportion of which will be present in the medium in correctly processed form, may be recovered from the medium by conventional procedures including separating the yeast cells from the medium by centrifugation, filtration or catching the insulin precursor by an ion exchange matrix or by a reverse phase absorption matrix, precipitating the proteinaceous components of the supernatant or filtrate by means of a salt, e.g. ammonium sulphate, followed by purification by a variety of chromatographic procedures, e.g. ion exchange chromatography, affinity chromatography, or the like.

The insulin precursors of the invention may be expressed with an N-terminal amino acid residue extension, as described in U.S. Pat. No. 5,395,922 and European Patent No. 765,395A, both of which patents are herein specifically incorporated by reference. The extension is found to be stably attached to the insulin precursor of the invention during fermentation, protecting the N-terminal end of the insulin precursor or insulin precursor analogue against the proteolytic activity of yeast proteases such as DPAP. The presence of an N-terminal extension on the insulin precursor may also serve as a protection of the N-terminal amino group during chemical processing of the protein, i.e. it may serve as a substitute for a BOC (t-butyl-oxycarbonyl) or similar protecting group. The N-terminal extension may be removed from the recovered insulin precursor by means of a proteolytic enzyme which is specific for a basic amino acid (e.g., Lys) so that the terminal extension is cleaved off at the Lys residue. Examples of such proteolytic enzymes are trypsin or *Achromobacter lyticus* protease.

After secretion to the culture medium and recovery, the insulin precursor of the invention will be subjected to various in vitro procedures to remove the possible N-terminal extension sequence and the mini C-peptide to give desB30 insulin. DesB30 insulin may then be converted into human insulin by adding a Thr in position B30. Conversion of the insulin precursor into human insulin by a suitable enzymatic conversion by means of trypsin or an *Achromobacter lyticus* protease in the presence of an L-threonine ester followed by conversion of the threonine ester of the insulin into insulin by basic or acid hydrolysis as described in U.S. Pat. No. 4,343,898 or U.S. Pat. No. 4,916,212 or Research Disclosure, September 1994/487 the disclosures of which are incorporated by reference hereinto. DesB30 insulin may also be converted into an acylated derivative as disclosed in U.S. Pat. No. 5,750,497 and U.S. Pat. No. 5,905,140 the disclosures of which are incorporated by reference hereinto.

As described below, insulin precursors with synthetic C-peptides were constructed featuring at least one Pro. *Saccharomyces cerevisiae* expression plasmids containing a polynucleotide sequence encoding the claimed insulin precursors were constructed by PCR and used to transform a *S. cerevisiae* host cell. The amount of expressed product was measured as a percentage of the amount of expressed control. The novel C-peptides of the invention gave increased yields of up to 100%.

The present invention is described in further detain in the following examples which are not in any way intended to limit the scope of the invention as claimed. The attached Figures are meant to be considered as integral parts of the specification and description of the invention. All references cited are herein specifically incorporated by reference for all that is described therein.

EXAMPLES

General Procedures

All expressions plasmids are of the C-POT type, similar to those described in EP 171, 142, which are characterized by containing the *Schizosaccharomyces pombe* triose phosphate isomerase gene (POT) for the purpose of plasmid selection and stabilization in *S. cerevisiae*. The plasmids also contain the *S. cerevisiae* triose phosphate isomerase promoter and terminator. These sequences are similar to the corresponding sequences in plasmid pKFN1003 (described in WO 90/100075) as are all sequences except the sequence of the EcoRI-XbaI fragment encoding the fusion protein of the leader and the insulin precursor product. In order to express different fusion proteins, the EcoRI-XbaI fragment of pKFN1003 is simply replaced by an EcoRI-XbaI fragment encoding the leader-insulin precursor-fusion of interest. Such EcoRI-XbaI fragments may be synthesized using synthetic oligonucleotides and PCR according to standard techniques.

Yeast transformants were prepared by transformation of the host strain *S. cerevisiae* strain MT663 (MATa/MATα pep4-3/pep4-3 HIS4/his4 tpi::LEU2/tpi::LEU2 Cir$^+$). The yeast strain MT663 was deposited in the Deutsche Sammlung von Mikroorganismen und Zellkulturen in connection with filing WO 92/11378 and was given the deposit number DSM 6278.

MT663 was grown on YPGaL (1% Bacto yeast extract, 2% Bacto peptone, 2% galactose, 1% lactate) to an O.D. at 600 nm of 0.6. 100 ml of culture was harvested by centrifugation, washed with 10 ml of water, recentrifuged and resuspended in 10 ml of a solution containing 1.2 M sorbitol, 25 mM Na$_2$EDTA pH=8.0 and 6.7 mg/ml dithiotreitol. The suspension was incubated at 30° C. for 15 minutes, centrifuged and the cells resuspended in 10 ml of a solution containing 1.2 M sorbitol, 10 mM Na$_2$EDTA, 0.1 M sodium citrate, pH 0 5.8, and 2 mg NOYOZYME®234. The suspension was incubated at 30° C. for 30 minutes, the cells collected by centrifugation, washed in 10 ml of 1.2 M sorbitol and 10 ml of CAS (1.2 M sorbitol, 10 mM CaCl$_2$, 10 mM Tris HCl (Tris=Tris(hydroxymethyl)aminomethane) pH=7.5) and resuspended in 2 ml of CAS. For transformation, 1 ml of CAS-suspended cells was mixed with approx. 0.1 mg of plasmid DNA and left at room temperature for 15 minutes. 1 ml of (20% polyethylene glycol 4000, 10 mM CaCl$_2$, 10 mM Tris HCl, pH=7.5) was added and the mixture left for a further 30 minutes at room temperature. The mixture was centrifuged and the pellet resuspended in 0.1 ml of SOS (1.2 M sorbitol, 33% v/v YPD, 6.7 mM CaCl$_2$) and incubated at 30° C. for 2 hours. The suspension was then centrifuged and the pellet resuspended in 0.5 ml of 1.2 M sorbitol. Then, 6 ml of top agar (the SC medium of Sherman et al. (1982) *Methods in Yeast Genetics*, Cold Spring Harbor Laboratory) containing 1.2 M sorbitol plus 2.5% agar) at 52° C. was added and the suspension poured on top of plates containing the same agar-solidified, sorbitol containing medium.

*S. cerevisiae* strain MT663 transformed with expression plasmids was grown in YPD for 72 h at 30° C. Quantitation of the insulin-precursor yield in the culture supernatants was performed by reverse-phase HPLC analysis with human insulin as an external standard (Snel & Damgaard (1988) Proinsulin heterogenity in pigs. Horm. Metabol. Res. 20:476–488).

Example 1

Synthetic genes encoding fusion proteins, consisting of the insulin precursor associated with a leader sequence consisting of a pre-peptide (signal peptide) and a pro-peptide, were constructed using PCR under standard conditions (Sambrook et al. (1989) Molecular Cloning, Cold Spring Harbor Laboratory Press) and E.H.F. polymerase (Boehringer Mannheim GmbH, Sandhoefer Strasse 116, Mannheim, Germany). The resulting DNA fragments were isolated and digested with endonucleases and purified using THE GENE CLEAN KIT® (Bio101 Inc., La Jolla, Calif., USA). Standard methods were used for DNA ligation and transformation of E. coli cells were performed by the CaCl$_2$ method (Sambrook et al. (1989) supra). Plasmids were purified from transformed E. coli cells using QIAGEN® columns (QIAGEN, Hilden, Germany). Nucleotide sequences were determined using the ALF Pharmacia Biotech DNA sequencing system with purified double-stranded plasmid DNA as template. Oligonucleotide primers for PCR were obtained from DNA technology (Århus, Denmark).

Secretion of the insulin precursor was facilitated by the TA57 leader or the TA39 leader (Kjeldsen et al., 1998. Protein Expression Purif. 14, 309–316), although a variety of known yeast leader sequences may be used.

Figure 1:
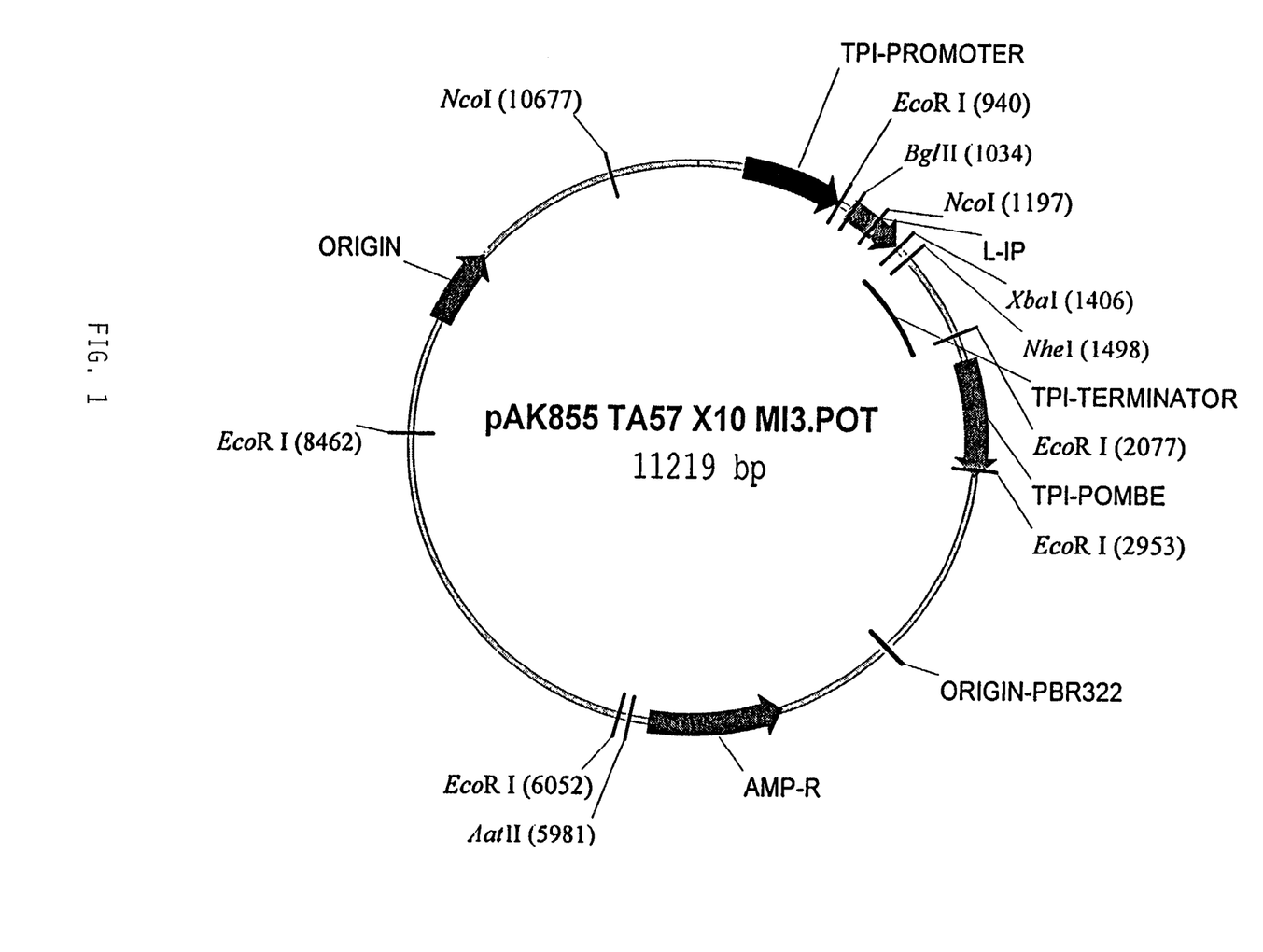
FIG. 1 represents the pAK855 *S. cerevisiae* expression plasmid expressing the TA57 leader-EEGEPK(SEQ ID NO:1)-B(1–29)-AlaAlaLys-A(1–21) precursor
Figure 2:
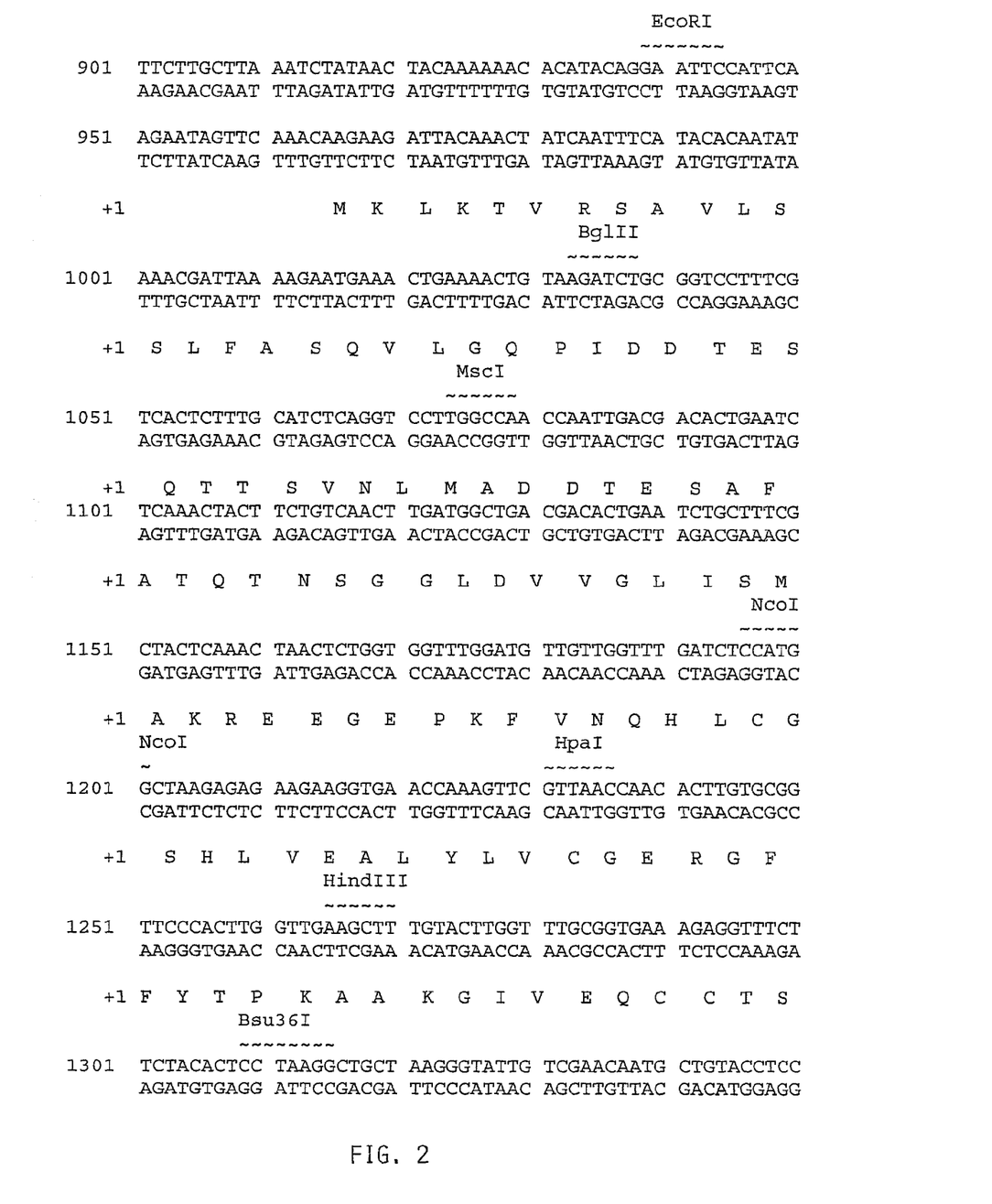
FIG. 2 represents the nucleotide sequence of the expression cassette of the pAK855 yeast expression plasmid and the inferred amino acid sequence (SEQ ID NO:2 and 3).

As shown in FIGS. 1 and 2, the pAK855 S. cerevisiae expression plasmid expressing the TA57 leader-EEGEDK (SEQ ID NO:1)-insulin precursor fusion protein was constructed based on the S. cerevisiae-E. coli shuttle POT plasmid (U.S. Pat. No. 5,871,957). In FIG. 1 L-IP indicates the fusion protein expression cassette encoding the leader-insulin precursor fusion protein; TPI-PROMOTER is the S. cerevisiae TPI1 promoter, TPI-TERMINATOR is the S. cerevisiae TPI1 terminator; TPI-POMBE indicates the S. pombe POT gene used for selection in S. cerevisiae; ORIGIN indicates a S. cerevisiae origin of replication derived from the 2 μm plasmid; AMP-R indicates the β-lactamase gene conferring resistance toward ampicillin, facilitating selection in E. coli; and ORIGIN-PBR322 indicates an E. coli origin of replication.

DNA encoding a number of fusions proteins of leader sequences and insulin precursors with different mini C-peptides was generated by PCR using appropriate oligonucleotides as primers, as described below. Standard methods were used to subclone DNA fragments encoding the leader-insulin precursor-fusion proteins into the CPOT expression vector in the following configuration: leader-Lys-Arg-spacer-insulin precursor, where Lys-Arg is a potential dibasic endoprotease processing site and spacer is an N-terminal extension. To optimize processing of the fusion protein by the S. cerevisiae Kex2 endoprotease, DNA encoding a spacer peptide (N-terminal extension), e.g. EEGEPK (SEQ ID NO:1), was inserted between the DNA encoding the leader and the insulin precursor (Kjeldsen, et al. 1999b. J. Biotechnology, 75, 195–208). However, the present of the spacer peptide is not mandatory. The insulin precursor was secreted as a single-chain N-terminally extended insulin precursor with a mini C-peptide, connecting Lys$^{B29}$ and Gly$^{41}$. After purification of the insulin precursor and proteolytic removal of the N-terminal extension and the mini C-peptide, the amino acid Thr$^{B30}$ can be added to Lys$^{B29}$ by enzyme-mediated transpeptidation, to generate human insulin (Markussen, et al. (1987) in "Peptides 1986" (Theodoropoulos, D., Ed.), pp. 189–194, Walter de Gruyter & Co., Berlin.).

Development of synthetic mini C-peptides was performed by randomization of one or more codon(s) encoding the amino acids in the mini C-peptide. The synthetic mini C-peptides feature typically an enzymatic processing site (Lys) at the C-terminus which allows enzymatic removal of the synthetic mini C-peptide. Randomization was performed using doped oligonucleotides which introduced codon(s) variations at one or more positions of the synthetic mini C-peptides. Typically one of the two primers (oligonucleotides) used for PCR was doped. An example of an oligonucleotides pair used for PCR generation of leader-insulin precursor with randomized synthetic mini C-peptides used to generated synthetic mini C-peptides with the general formula: Xaa-Pro-Lys (XPK) are as follows:

Primer A:

```
5'-TTGCTTAAATCTATAACTAC-3'     (SEQ ID NO: 4)
```

Primer B:

```
                                              (SEQ ID NO:5)
5'-TTAGTTTCTAGACTAGTTGCAGTAGTTTTCCAATTGGTACAAGGAGC

AGATGGAGGTACAGCATTGTTCGACAATACCCTTTGGMNNCTTAGGAGTG

TAGAAGAA-3'
```

N=ACTG

M=AC

Polymerase chain reaction. PCR was typically performed as indicated below: 5 μl Primer A (20 pmol), 5 μl Primer B (20 pmol), 10 μl 10×PCR buffer, 8 μl dNTP mix, 0.75 μl E.H.F. enzyme, 1 μl pAK855 plasmid as template (approximately 0.2 μg DNA) and 70.25 μl distilled water.

Typically between 10 and 15 cycles were performed, one cycle typically was 95° C. for 45 sec.; 55° C. for 1 min; 72° C. for 1.5 min. The PCR mixture was subsequently loaded onto a 2% agarose gel and electrophoresis was performed using standard techniques. The resulting DNA fragment was cut out of agarose gel and isolated by THE GENE CLEAN KIT®.

FIG. 2 shows the nucleotide sequence of pAK855 DNA expression cassette used as template for PCR and inferred amino acids of the encoded fusion protein (TA57-leader-EEGEPK(SEQ ID NO:1)-insulin precursor of pAK855 (SEQ ID NO: 2 and 3).

Likewise expression cassettes encoding a fusion protein TA39-leader-EEGEEPK(SEQ ID NO:1)-insulin precursor The purified PCR DNA fragment was dissolved in water and restriction endonucleases buffer and digested with suitable restriction endonucleases (e.g. Bgl II and Xba I) according to standard techniques. The BglII-XbaI DNA fragments were subjected to agarose electrophoresis and purified using THE GENE CLEAN KIT®.

The digested and isolated DNA fragments were ligated together with a suitable vector (e.g. of the CPOT type) using T4 DNA ligase and standard conditions. The ligation mix was subsequently transformed into a competent E. coli strain followed by selection with ampicillin resistance. Plasmids from the resulting E. coli's were isolated using QIAGEN® columns.

The plasmids were subsequently used for transformation of a suitable S. cerevisiae host strain, e.g., MT663 (MATa/MATα pep4-3/pep4-3 HIS4/his4 tpi::LEU2/tpi::LEU2 Cir$^+$). Individual transformed S. cerevisiae clones were grown in liquid culture, and the quantity of the insulin precursor secreted to the culture supernatants was determined by RP-HPLC. The DNA sequence encoding the synthetic mini C-peptide of the expression plasmids from *S. cerevisiae* clones secreting increased quantity of the insulin precursor were then determined. Subsequently, the identified synthetic mini C-peptide sequence might be subjected to another round of randomization optimization.

Table 1 shows the insulin precursors generated by the above method and production yield expressed as a percent of control. Fermentation was conducted at 30° C. for 72 h in 5 ml YPD. Yield of the insulin precursor was determined by RP-HPLC of the culture supernatant, and is expressed relative to the yield of a control strain expressing a leader-insulin precursor fusion protein in which the B29 residue is linked to the A1 residue by a mini C-peptide Ala-Ala-Lys. YAP3 is the YAP3 signal sequence. The sequence EEGEPK (SEQ ID NO:1) is an N-terminal extension to the B-chain and TA57 is a synthetic pro-sequence QPIDDTESQTTS-VNLMADDTESAFATQTNSGGLDVVGLISMAKR (SEQ ID NO:6).

TABLE 1

| Leader-N-terminal extension | Precursor | mini C-peptide | Yield* |
|---|---|---|---|
| YAP3-TA57-EEGEPK IP (control) (SEQ ID NO:1) | | AlaAlaLys | 100 |
| YAP3-TA57-EEGEPK IP (SEQ ID NO:1) | | GlnProLys | 190 |
| YAP3-TA57-EEGEPK IP (SEQ ID NO:1) | | ThrProLys | 125 |
| YAP3-TA57-EEGEPK IP (SEQ ID NO:1) | | GluProLys | 164 |
| YAP3-TA57-EEGEPK IP (SEQ ID NO:1) | | GlyProLys | 120 |
| YAP3-TA57-EEGEPK IP (SEQ ID NO:1) | | MetProLys | 118 |
| YAP3-TA57-EEGEPK IP (SEQ ID NO:1) | | SerProLys | 107 |
| YAP3-TA57-EEGEPK IP (SEQ ID NO:1) | | AspProLys | 187 |

Example 2

By procedures analogue to the procedures described in Example 1, insulin precursors with a Pro in the mini C-peptide under the control of the synthetic leader TA37 QPIDDTESNTTSVNLMADDTESRFATNT-TLAGGLDVVNLI-SMAKR (SEQ ID NO:7) and the YAP3 signal sequence were expressed in the yeast host MT663. The precursors all comprised an N-terminal extension EEGEPK (SEQ ID NO:1). The increase in expression yield compared to a control is shown in Table 2.

TABLE 2

| Leader-N-terminal extension | Precursor | mini C-peptide | Yield* |
|---|---|---|---|
| YAP3-TA39-EEGEPK (SEQ ID NO:1) | IP (control) | AlaAlaLys | 100 |
| YAP3-TA39-EEGEPK (SEQ ID NO:1) | IP | SerAspProLys (SEQ ID NO:8) | 124 |
| YAP3-TA39-EEGEPK (SEQ ID NO:1) | IP | AsnAspProLys (SEQ ID NO:9) | 135 |
| YAP3-TA39-EEGEPK (SEQ ID NO:1) | IP | GluAspProLys (SEQ ID NO:10) | 130 |
| YAP3-TA39-EEGEPK (SEQ ID NO:1) | IP | AlaAspProLys (SEQ ID NO:11) | 130 |

Example 3

By procedures analogue to the procedures described in Example 1, insulin precursors with a Pro in the mini C-peptide under the control of the α-factor leader sequence were expressed in the yeast host MT663. The insulin precursors were expressed with and without an N-terminal extension EEAEAEAPK (SEQ ID NO:12). The increase in expression yield compared to a control is shown in Table 3.

TABLE 3

| Leader-N-terminal extension | Precursor | mini C-peptide | Yield* |
|---|---|---|---|
| α-factor-EEAEAEAPK (SEQ ID NO:12) | IP (control) | AlaAlaLys | 100 |
| α-factor-EEAEAEAPK (SEQ ID NO:12) | IP | AspProLys | 211 |
| α-factor | IP | AspProLys | 289 |

What is claimed is:

1. An insulin precursor comprising the formula

B(1–29)-X$_1$-Y-A(1–21)

wherein
B(1–29) is a natural insulin B chain lacking the B30 amino acid residue and A(1–21) is a natural insulin A chain;
X$_1$ is a peptide sequence of 1–5 amino acid residues of which at least one is Pro and
Y is a cleavage site;
and said at least one Pro is immediately N-terminal to Y.

2. An insulin precursor according to claim 1, wherein X$_1$ is 1–4 amino acid residues.

3. An insulin precursor according to claim 1, wherein X$_1$ is 1, 2, or 3 amino acid residues.

4. An insulin precursor according to claim 1, wherein Y is Lys or Arg.

5. An insulin precursor according to claim 1, wherein X$_1$ is GluPro and Y is Lys.

6. An insulin precursor according to claim 1, wherein X$_1$ is AspPro and Y is Lys.

7. An insulin precursor according to claim 1, wherein X$_1$ is GlnPro and Y is Lys.

8. A polynucleotide sequence encoding an insulin precursor with the formula

B(1–29)-X$_1$-Y-A(1–21)

wherein
B(1–29) is a natural insulin B chain lacking the B30 amino acid residue and A(1–21) is a natural insulin A chain;
X$_1$ is a peptide sequence of 1–5 amino acid residues of which as least one is Pro; and
Y is a cleavage site, and wherein said at least one Pro is immediately N-terminal to Y.

9. A polynucleotide sequence according to claim 8, wherein X$_1$ is 1, 2, 3, or 4 amino acid residues.

10. A polynucleotide sequence according to claim 8, wherein X$_1$ is GluPro and Y is Lys.

11. A polynucleotide sequence according to claim 8, wherein X$_1$ is AspPro and Y is Lys.

12. A polynucleotide sequence according to claim 8, wherein X$_1$ is GlnPro and Y is Lys.

13. A polynucleotide sequence according to claim 8, wherein Y is Lys or Arg.

14. An expression vector comprising a polynucleotide sequence according to claim 8.

15. A host cell comprising a vector according to claim 14.

16. A host cell comprising a polynucleotide sequence according to claim 8.

17. A method for making an insulin precursor, said method comprising
(i) culturing a host cell comprising a polynucleotide sequence encoding an insulin precursor with the formula

B(1–29)-X$_1$-Y-A(1–21)

wherein
B(1–29) is a natural insulin B chain lacking the B30 amino acid residue and A(1–21) is a natural insulin A chain;
X$_1$ is a peptide sequence of 1–5 amino acid residues of which at least one is Pro; and
Y is a cleavage site, and said at least one Pro is immediately N-terminal to Y, under suitable culture conditions for expression of said insulin precursor; and
(ii) recovering the expressed insulin precursor.

18. A method according to claim 17, wherein X$_1$ is 1–4 amino acid residues.

19. A method according to claim 17, wherein X$_1$ is 1–3 amino acid residues.

20. A method according to claim 17, wherein X$_1$ is 1 or 2 amino acid residues.

21. A method according to claim 17, wherein X$_1$ is GluPro and Y is Lys.

22. A method according to claim 17, wherein X$_1$ is AspPro and Y is Lys.

23. A method according to claim 17, wherein X$_1$ is GlnPro and Y is Lys.

24. A method according to claim 17, wherein Y is Lys or Arg.

25. A method according to claim 17, wherein the host cell is a yeast cell.

26. A method for making desB30 human insulin or human insulin, said method comprising
(i) culturing a host cell comprising a polynucleotide sequence encoding an insulin precursor with the formula

B(1–29)-X$_1$-Y-A(1–21)

wherein
B(1–29) is a natural insulin B chain lacking the B30 amino acid residue and A(1–21) is a natural insulin A chain;
X$_1$ is a peptide sequence of 1–5 amino acid residues of which at least one is Pro and
Y is a cleavage site;
and wherein said at least one Pro is immediately N-terminal to Y, under suitable culture conditions for expression of said insulin precursor;
(ii) recovering the insulin precursor from the culture medium, and
(iii) converting the insulin precursor into desB30 human insulin or human insulin by in vitro chemical or enzymatic conversion.

27. A method according to claim 26, wherein X$_1$ is 1–4 amino acid residues.

28. A method according to claim 26, wherein X$_1$ is 1–3 amino acid residues.

29. A method according to claim 26, wherein X$_1$ is 1 or 2 amino acid residues.

30. A method according to claim 26, wherein X$_1$ is GluPro and Y is Lys.

31. A method according to claim 26, wherein X$_1$ is AspPro and Y is Lys.

32. A method according to claim 26, wherein X$_1$ is GlnPro and Y is Lys.

33. A method according to claim 26, wherein Y is Lys or Arg.

34. A method according to claim 26, wherein the host cell is a yeast host cell.

35. An insulin precursor comprising a connecting peptide (C-peptide) being cleavable from the A and B chains, wherein said connecting peptide comprises at least one Pro and a cleavage site enabling cleavage of the peptide bond between the A-chain and the connecting peptide and wherein said at least one Pro is immediately N-terminal to said cleavage site.

36. An insulin precursor according to claim 35, wherein the connecting peptide is of up to 10 amino acid residues in length.

37. An insulin precursor comprising a connecting peptide (C-peptide) being cleavable from the A and B chains, wherein said connecting peptide comprises at least one Pro and wherein the connecting peptide is of up to 6 amino acid residues in length and wherein said at least one Pro is immediately N-terminal to Y.

* * * * *

SEQUENCE LISTING

<160> NUMBER OF SEQ ID NOS: 12

<210> SEQ ID NO 1
<211> LENGTH: 6
<212> TYPE: PRT
<213> ORGANISM: Artificial Sequence -continued

```
<220> FEATURE:
<223> OTHER INFORMATION: N-terminal sequence

<400> SEQUENCE: 1

Glu Glu Gly Glu Pro Lys
 1               5

<210> SEQ ID NO 2
<211> LENGTH: 550
<212> TYPE: DNA
<213> ORGANISM: Artificial Sequence
<220> FEATURE:
<223> OTHER INFORMATION: Synthetic
<221> NAME/KEY: CDS
<222> LOCATION: (115)...(486)

<400> SEQUENCE: 2
ttcttgctta aatctataac tacaaaaaac acatacagga attccattca agaatagttc      60
aaacaagaag attacaaact atcaatttca tacacaatat aaacgattaa aaga atg      117
                                                             Met
                                                              1 aaa ctg aaa act gta aga tct gcg gtc ctt tcg tca ctc ttt gca tct      165
Lys Leu Lys Thr Val Arg Ser Ala Val Leu Ser Ser Leu Phe Ala Ser
        5                  10                 15 cag gtc ctt ggc caa cca att gac gac act gaa tct caa act act tct      213
Gln Val Leu Gly Gln Pro Ile Asp Asp Thr Glu Ser Gln Thr Thr Ser
         20                 25                 30 gtc aac ttg atg gct gac gac act gaa tct gct ttc gct act caa act      261
Val Asn Leu Met Ala Asp Asp Thr Glu Ser Ala Phe Ala Thr Gln Thr
 35                 40                 45 aac tct ggt ggt ttg gat gtt gtt ggt ttg atc tcc atg gct aag aga      309
Asn Ser Gly Gly Leu Asp Val Val Gly Leu Ile Ser Met Ala Lys Arg
 50                 55                 60                 65 gaa gaa ggt gaa cca aag ttc gtt aac caa cac ttg tgc ggt tcc cac      357
Glu Glu Gly Glu Pro Lys Phe Val Asn Gln His Leu Cys Gly Ser His
                 70                 75                 80 ttg gtt gaa gct ttg tac ttg gtt tgc ggt gaa aga ggt ttc ttc tac      405
Leu Val Glu Ala Leu Tyr Leu Val Cys Gly Glu Arg Gly Phe Phe Tyr
             85                 90                 95 act cct aag gct gct aag ggt att gtc gaa caa tgc tgt acc tcc atc      453
Thr Pro Lys Ala Ala Lys Gly Ile Val Glu Gln Cys Cys Thr Ser Ile
        100                105                110 tgc tcc ttg tac caa ttg gaa aac tac tgc aac tagacgcagc ccgcaggctc    506
Cys Ser Leu Tyr Gln Leu Glu Asn Tyr Cys Asn
    115                120 tagaaactaa gattaatata attatataaa aatattatct tctt                     550

<210> SEQ ID NO 3
<211> LENGTH: 124
<212> TYPE: PRT
<213> ORGANISM: Artificial Sequence
<220> FEATURE:
<223> OTHER INFORMATION: Synthetic

<400> SEQUENCE: 3

Met Lys Leu Lys Thr Val Arg Ser Ala Val Leu Ser Ser Leu Phe Ala
 1               5                  10                  15

Ser Gln Val Leu Gly Gln Pro Ile Asp Asp Thr Glu Ser Gln Thr Thr
             20                  25                  30
```

-continued

Ser Val Asn Leu Met Ala Asp Asp Thr Glu Ser Ala Phe Ala Thr Gln
        35                  40                  45

Thr Asn Ser Gly Gly Leu Asp Val Val Gly Leu Ile Ser Met Ala Lys
 50                  55                  60

Arg Glu Glu Gly Glu Pro Lys Phe Val Asn Gln His Leu Cys Gly Ser
 65                  70                  75                  80

His Leu Val Glu Ala Leu Tyr Leu Val Cys Gly Glu Arg Gly Phe Phe
                 85                  90                  95

Tyr Thr Pro Lys Ala Ala Lys Gly Ile Val Glu Gln Cys Cys Thr Ser
             100                 105                 110

Ile Cys Ser Leu Tyr Gln Leu Glu Asn Tyr Cys Asn
        115                 120

<210> SEQ ID NO 4
<211> LENGTH: 20
<212> TYPE: DNA
<213> ORGANISM: Artificial Sequence
<220> FEATURE:
<223> OTHER INFORMATION: Synthetic

<400> SEQUENCE: 4
ttgcttaaat ctataactac                                              20

<210> SEQ ID NO 5
<211> LENGTH: 105
<212> TYPE: DNA
<213> ORGANISM: Artificial Sequence
<220> FEATURE:
<223> OTHER INFORMATION: Synthetic
<221> NAME/KEY: misc_feature
<222> LOCATION: (1)...(105)
<223> OTHER INFORMATION: n = A,T,C or G
      m = A or C

<400> SEQUENCE: 5
ttagtttcta gactagttgc agtagttttc caattggtac aaggagcaga tggaggtaca      60
gcattgttcg acaatacCct ttggmnnctt aggagtgtag aagaa                    105

<210> SEQ ID NO 6
<211> LENGTH: 44
<212> TYPE: PRT
<213> ORGANISM: Artificial Sequence
<220> FEATURE:
<223> OTHER INFORMATION: Synthetic

<400> SEQUENCE: 6

Gln Pro Ile Asp Asp Thr Glu Ser Gln Thr Thr Ser Val Asn Leu Met
 1               5                  10                  15

Ala Asp Asp Thr Glu Ser Ala Phe Ala Thr Gln Thr Asn Ser Gly Gly
                 20                  25                  30

Leu Asp Val Val Gly Leu Ile Ser Met Ala Lys Arg
         35                  40

<210> SEQ ID NO 7
<211> LENGTH: 45
<212> TYPE: PRT
<213> ORGANISM: Artificial Sequence
<220> FEATURE:
<223> OTHER INFORMATION: Synthetic

```
<400> SEQUENCE: 7

Gln Pro Ile Asp Asp Thr Glu Ser Asn Thr Thr Ser Val Asn Leu Met
  1               5                  10                  15

Ala Asp Asp Thr Glu Ser Arg Phe Ala Thr Asn Thr Thr Leu Ala Gly
             20                  25                  30

Gly Leu Asp Val Val Asn Leu Ile Ser Met Ala Lys Arg
         35                  40                  45

<210> SEQ ID NO 8
<211> LENGTH: 4
<212> TYPE: PRT
<213> ORGANISM: Artificial Sequence
<220> FEATURE:
<223> OTHER INFORMATION: C-peptide

<400> SEQUENCE: 8

Ser Asp Pro Lys
  1

<210> SEQ ID NO 9
<211> LENGTH: 4
<212> TYPE: PRT
<213> ORGANISM: Artificial Sequence
<220> FEATURE:
<223> OTHER INFORMATION: Synthetic

<400> SEQUENCE: 9

Asn Asp Pro Lys
  1

<210> SEQ ID NO 10
<211> LENGTH: 4
<212> TYPE: PRT
<213> ORGANISM: Artificial Sequence
<220> FEATURE:
<223> OTHER INFORMATION: C-peptide

<400> SEQUENCE: 10

Glu Asp Pro Lys
  1

<210> SEQ ID NO 11
<211> LENGTH: 4
<212> TYPE: PRT
<213> ORGANISM: Artificial Sequence
<220> FEATURE:
<223> OTHER INFORMATION: C-peptide

<400> SEQUENCE: 11

Ala Asp Pro Lys
  1

<210> SEQ ID NO 12
<211> LENGTH: 9
<212> TYPE: PRT
<213> ORGANISM: Artificial Sequence
<220> FEATURE:
<223> OTHER INFORMATION: Synthetic

<400> SEQUENCE: 12

Glu Glu Ala Glu Ala Glu Ala Pro Lys
  1               5
```